United States Patent
Lyons et al.

(10) Patent No.: US 6,379,703 B1
(45) Date of Patent: *Apr. 30, 2002

(54) PREPARATION OF MICROPARTICLES HAVING A SELECTED RELEASE PROFILE

(75) Inventors: Shawn L. Lyons, Cincinnati; J. Michael Ramstack, Lebanon; Steven G. Wright, Madeira, all of OH (US)

(73) Assignee: Alkermes Controlled Therapeutics Inc., II, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/722,335

(22) Filed: Nov. 28, 2000

Related U.S. Application Data

(63) Continuation of application No. 09/223,276, filed on Dec. 30, 1998, now Pat. No. 6,194,006.

(51) Int. Cl.[7] .............................. A61K 9/14; B01J 13/02; D21B 1/04; B29C 67/00; B29C 59/00
(52) U.S. Cl. ...................... 424/489; 264/4.1; 264/4.21; 264/115; 264/117; 264/122; 514/772.3
(58) Field of Search ............................ 424/489; 264/4.1, 264/4.21, 115, 117, 122; 514/772.3

(56) References Cited

U.S. PATENT DOCUMENTS

| | | |
|---|---|---|
| 3,523,906 A | 8/1970 | Vrancken et al. |
| 3,691,090 A | 9/1972 | Kitajima et al. |
| 3,737,337 A | 6/1973 | Schnoring et al. |
| 3,773,919 A | 11/1973 | Boswell et al. |
| 3,891,570 A | 6/1975 | Fukushima et al. |
| 3,960,757 A | 6/1976 | Morishita et al. |
| 4,221,862 A | 9/1980 | Naito et al. |
| 4,384,975 A | 5/1983 | Fong |
| 4,389,330 A | 6/1983 | Tice et al. |
| 4,530,840 A | 7/1985 | Tice et al. |

(List continued on next page.)

FOREIGN PATENT DOCUMENTS

| | | |
|---|---|---|
| EP | 0 486 959 A1 | 5/1992 |
| EP | 0831773 | 12/1999 |
| WO | WO 89/03678 | 5/1989 |
| WO | WO 90/13361 | 11/1990 |
| WO | WO 94/10982 | 5/1994 |
| WO | WO 95/13799 | 5/1995 |
| WO | WO 96/40049 | 12/1996 |
| WO | WO 97/41837 | 11/1997 |
| WO | WO 99/12549 | 3/1999 |

OTHER PUBLICATIONS

B. Conti et al., "Use of polylactic acid for the preparation of microparticulate drug delivery systems, " J. Microencapsulation 1992, vol. 9, No. 2, pp. 153–166, XP 000259942.

Y.F. Maa et al., "Liquid–liquid emulsidication by static mixers for use in microencapsulation," J. Microencapsulation, 1996, vol. 13, No. 4, pp. 419–433, XP 000589904.

Baker, J.R., "Motionless Mixers Stir Up New Uses," *Chemical Engineering Progress*, pp. 32–38 (Jun. 1991).

(List continued on next page.)

*Primary Examiner*—Thurman K. Page
*Assistant Examiner*—S. Tran
(74) *Attorney, Agent, or Firm*—Andrea G. Reister; Covington & Burling

(57) ABSTRACT

An improved method for preparing microparticles that exhibit controlled release of an effective amount of an active agent over an extended period of time. More particularly, a method is provided for preparing microparticles having a selected release profile for release of active agent contained in the microparticles. By adjusting the degree of drying that is performed during the preparation of the microparticles, the release profile can be controlled. By performing no intermediate drying, an initial burst and a substantially linear release profile is achieved. By performing substantially complete intermediate drying, an initial lag phase and a substantially sigmoidal release profile is achieved.

18 Claims, 6 Drawing Sheets

U.S. PATENT DOCUMENTS

| | | | |
|---|---|---|---|
| 4,940,588 A | | 7/1990 | Sparks et al. |
| 5,066,436 A | | 11/1991 | Komen et al. |
| 5,407,609 A | | 4/1995 | Tice et al. |
| 5,478,564 A | | 12/1995 | Wantier et al. |
| 5,541,172 A | | 7/1996 | Labric et al. |
| 5,650,173 A | * | 7/1997 | Ramstack et al. .......... 424/489 |
| 5,654,008 A | | 8/1997 | Herbert et al. |
| 5,688,801 A | | 11/1997 | Mesens et al. |
| 5,770,231 A | | 6/1998 | Mesens et al. |
| 5,792,477 A | | 8/1998 | Rickey et al. |
| 5,851,538 A | * | 12/1998 | Froix et al. ................. 424/401 |
| 5,945,126 A | | 8/1999 | Thanoo et al. |
| 6,013,853 A | * | 1/2000 | Athanasiou et al. .......... 623/11 |

OTHER PUBLICATIONS

Beck, L.R. et al., Biology of Reproduction, 28:186–195 (Feb. 1983).

Bodmeier, R., et al., International Journal of Pharmaceuticals, 43:179–186 (1988).

R. Jalil et al., Journal of Microencapsulation, vol. 7, no. 3, Jul.–Sep. 1990, pp. 297–319.

Wen–I Li et al., Journal of Controlled Release, 37:199–214 (Dec. 1995).

H. V. Maulding et al., "Biodegradable Microcapsules: Acceleration of Polymeric Excipient Hydrolytic Rate by Incorporation of a Basic Medicament," Journal of Controlled Release, 3:103–117 (Mar. 1986).

Mutsakis, M., et al., "Advances in Static Mixing Technology," *Chemical Engineering Progress*, pp. 42–48 (Jul. 1986).

Hongkee Sah et al., Pharmaceutical Research, 13:360–367 (Mar. 1996).

Toyomi Sato et al., Pharamaceutical Research, 5:21–30 (1988).

* cited by examiner

PREPARATION OF MICROPARTICLES HAVING A SELECTED RELEASE PROFILE

CROSS REFERENCE TO RELATED APPLICATIONS

The present application is a continuation of application Ser. No. 09/223,276, filed Dec. 30, 1998 now U.S. Pat. No. 6,194,056.

BACKGROUND OF THE INVENTION

1. Field of the Invention

The present invention related to preparation of microparticles containing an active agent. More particularly, the present invention relates to microparticles having a selected release profile for release of the active agent from the microparticles, and to a method for the preparation of such microparticles.

2. Related Art

A variety of methods is known by which compounds can be encapuslated in the form of microparticles. It is particularly advantageous to encapsulate a biologically active or pharmaceutically active agent within a biocompatible, biodegradable wall-forming material (e.g., a polymer) to provide sustained or delayed release of drugs or other active agents. In these methods, the material to be encapsulated (drugs or other active agents) is generally dissolve, dispersed, or emulsified in a solvent containing the wall forming material. Solvent is then removed from the microparticles to form the finished microparticle product.

An example of a conventional microencapsulation process is disclosed in U.S. Pat. No. 3,737,337 wherein a solution of a wall or shell forming polymeric material in a solvent is prepared. The solvent is only partially miscible in water. A solid or core material is dissolved or dispersed in the polymer-containing solution and, thereafter, the core-material-polymer-containing solution is dispersed in an aqueous liquid that is immiscible in the organic solvent in order to remove solvent from the microparticles.

Tice et al. in U.S. Pat. No. 4,389,330 describe the preparation of microparticles containing an active agent by using a two-step solvent removal process. In the Tice et al. process, the active agent and the polymer are dissolved in a solvent The mixture of ingredients in the solvent is then emulsified in a continuous-phase processing medium that is immiscible with the solvent. A dispersion of microparticles containing the indicated ingredients is formed in the continuous-phase medium by mechanical agitation of the mixed materials. From this dispersion, the organic solvent can be partially removed in the first step of the solvent removal process. After the first stage, the dispersed microparticles are isolated from the continuous-phase processing medium by any convenient means of separation. Following the isolation, the remainder of the solvent in the microparticles is removed by extraction. After the remainder of the solvent has been removed from the microparticles, they are dried by exposure to air or by other conventional drying techniques.

Another conventional method of microencapsulating an agent to form a microencapsulated product is disclosed in U.S. Pat. No. 5,407,609. This method includes: (1) dissolving or otherwise dispersing one or more agents (liquids or solids) in a solvent containing one or more dissolved wall-forming materials or excipients (usually the wall-forming material or excipient is a polymer dissolved in a polymer solvent); (2) dispersing the agent/polymer-solvent mixture (the discontinuous phase) into a processing medium (the continuous phase which is preferably saturated with polymer solvent) to form an emulsion; and (3) transferring all of the emulsion immediately to a large volume of processing medium or other suitable extraction medium, to immediately extract the solvent from the microdroplets in the emulsion to form a microencapsulated product, such as microcapsules or microspheres.

U.S. Pat. No. 5,650,173, the entirety of which is incorporated herein by reference, discloses a process for preparing biodegradable, biocompatible microparticles comprising a biodegradable, biocompatible polymeric binder and a biologically active agent, wherein a blend of at least two substantially non-toxic solvents, free of halogenated hydrocarbons, are used to dissolve both the agent and the polymer. The solvent blend containing the dissolved agent and polymer is dispersed in an aqueous solution to form droplets. The resulting emulsion is added to an aqueous extraction medium preferably containing at least one of the solvents of the blend, whereby the rate of extraction of each solvent is controlled, whereupon the biodegradable, biocompatible microparticles containing the biologically active agent are formed. Active agents suitable for encapsulation by this process include, but are not limited to, norethindrone, risperidone, and testosterone, and a preferred solvent blend is one comprising benzyl alcohol and ethyl acetate.

U.S. Pat. No. 5,654,008, the entirety of which is incorporated herein by reference, describes a microencapsulation process that uses a static mixer. A first phase, comprising an active agent and a polymer, and a second phase are pumped through a static mixer into a quench liquid to form microparticles containing the active agent.

The documents described above all disclose methods that can be used to prepare microparticles that contain an active agent. As explained, for example, in U.S. Pat. No. 5,650,173, by appropriately selecting the polymeric materials, a microparticle formulation can be made in which the resulting microparticles exhibit both diffusional release and biodegradation release properties. For a diffusional mechanism of release, the active agent is released from the microparticles prior to substantial degradation of the polymer. The active agent can also be released from the microparticles as the polymeric excipient erodes. However, none of the foregoing documents disclose a specific method for preparing microparticles that have a selected release profile for release of the active agent from the microparticles.

Thus, there is a need in the art for a method for preparing microparticles having a selected release profile for release of active agent in the microparticles in accordance with the selected release profile. There is a further need in the art for a method for controlling the release profile of the active agent contained in microparticles. The present invention, the description of which is fully set forth below, solves the need in the art for such methods.

SUMMARY OF THE INVENTION

The present invention relates to an improved method for preparing microparticles that exhibit controlled release of an effective amount of an active agent over an extended penrod of time. More particularly, the present invention relates to a method for preparing microparticles having a selected release profile for release of active agent contained in the microparticles. In one aspect, the method of the present invention comprises: preparing an emulsion that comprises a first phase and a second phase, the first phase comprising the active agent, a polymer, and a solvent for the polymer;

quenching the emulsion in a quench liquid to form microparticles containing the active agent; and performing a degree of intermediate drying of the microparticles so that the selected release profile is achieved. If the degree of intermediate drying performed is no intermediate drying, then the resulting microparticles have an initial burst and a substantially linear release profile. If the degree of intermediate drying performed is substantially complete intermediate drying, then the resulting microparticles have an initial lag phase and a substantially sigmoidal release profile.

In a further aspect of the present invention, the method further comprises, after the intermediate drying step, the steps of washing the microparticles and final drying the microparticles. In a preferred aspect of the invention, the washing step is carried out by: introducing the microparticles into a vessel containing an extraction medium having a temperature lower than the glass transition temperature of the microparticles; agitating the vessel contents to disperse the microparticles in the extraction medium; and transferring the microparticles from the vessel to an extraction tank having another extraction medium having a temperature higher than the glass transition temperature of the microparticles at the time of transfer of the microparticles.

In yet another aspect of the invention, a method for controlling a release profile of an active agent contained in microparticles is provided. The method comprises: forming microparticles containing the active agent by quenching an emulsion in a quench liquid, the emulsion comprising a first phase and a second phase, the first phase comprising the active agent, a polymer, and a solvent for the polymer; and adjusting a degree of drying of the microparticles, the degree of drying affecting the release profile of the active agent from the microparticles. In a further aspect, the degree of drying is adjusted to comprise no intermediate drying, thereby resulting in an initial burst of the active agent and a substantially linear release of the active agent. In another aspect, the degree of drying is adjusted to comprise substantially complete intermediate drying, thereby resulting in an initial lag in release of the active agent and a substantially sigmoidal release of the active agent. In still a further aspect of the invention, the adjusting step comprises: performing a degree of intermediate drying of the microparticles; washing the microparticles; and performing final drying of the microparticles. In yet another aspect of the invention, the washing step comprises: introducing the microparticles into a vessel containing an extraction medium having a temperature lower than the glass transition temperature of the microparticles; agitating the vessel contents to disperse the microparticles in the extraction medium; and transferring the microparticles from the vessel to an extraction tank having another extraction medium having a temperature higher than the glass transition temperature of the microparticles at the time of transfer of the microparticles.

In still a further aspect of the present invention, a microencapsulated active agent having a selected release profile is provided. The microencapsulated active agent is prepared by a method for preparing microparticles, which method comprises: preparing an emulsion that comprises a first phase and a second phase, the first phase comprising the active agent, a polymer, and a solvent for the polymer; quenching the emulsion in a quench liquid to form microparticles containing the active agent; and performing a degree of intermediate drying of the microparticles so that the selected release profile of the active agent from the microparticles is achieved.

Features and Advantages

Advantages of the method of the present invention are that it provides, inter alia, a biodegradable, biocompatible system that can be injected into a patient, the ability to mix microparticles containing different active agents, and the ability to program release by preparing microparticles with selected release profiles and with multiphasic release patterns to give faster or slower rates of active agent release as needed.

A particular advantage of the method of the present invention is that it provides an additional parameter, the degree of intermediate drying, to control the release pattern or profile of microparticles. The method of the present invention is advantageous in that after such parameters as monomer size, coreload, and molecular weight have been determined, the release profile can be adjusted through the degree of intermediate drying.

An advantage of the products prepared by the method of the present invention is that durations of action ranging from several days to more than 200 days can be obtained, depending upon the type of microparticle and release profile selected. In preferred embodiments, the microparticles are designed to afford treatment to patients during duration of action periods of 30 to 100 days. A 60 day duration of action period is considered to be particularly advantageous. As readily apparent to one of skill in the relevant art, the duration of action can be controlled by manipulation of the polymer composition, polymer:drug ratio, microparticle size, excipients, and concentration of residual solvent remaining in the microparticle.

BRIEF DESCRIPTION OF THE FIGURES

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENTS

Overview

Figure 1:
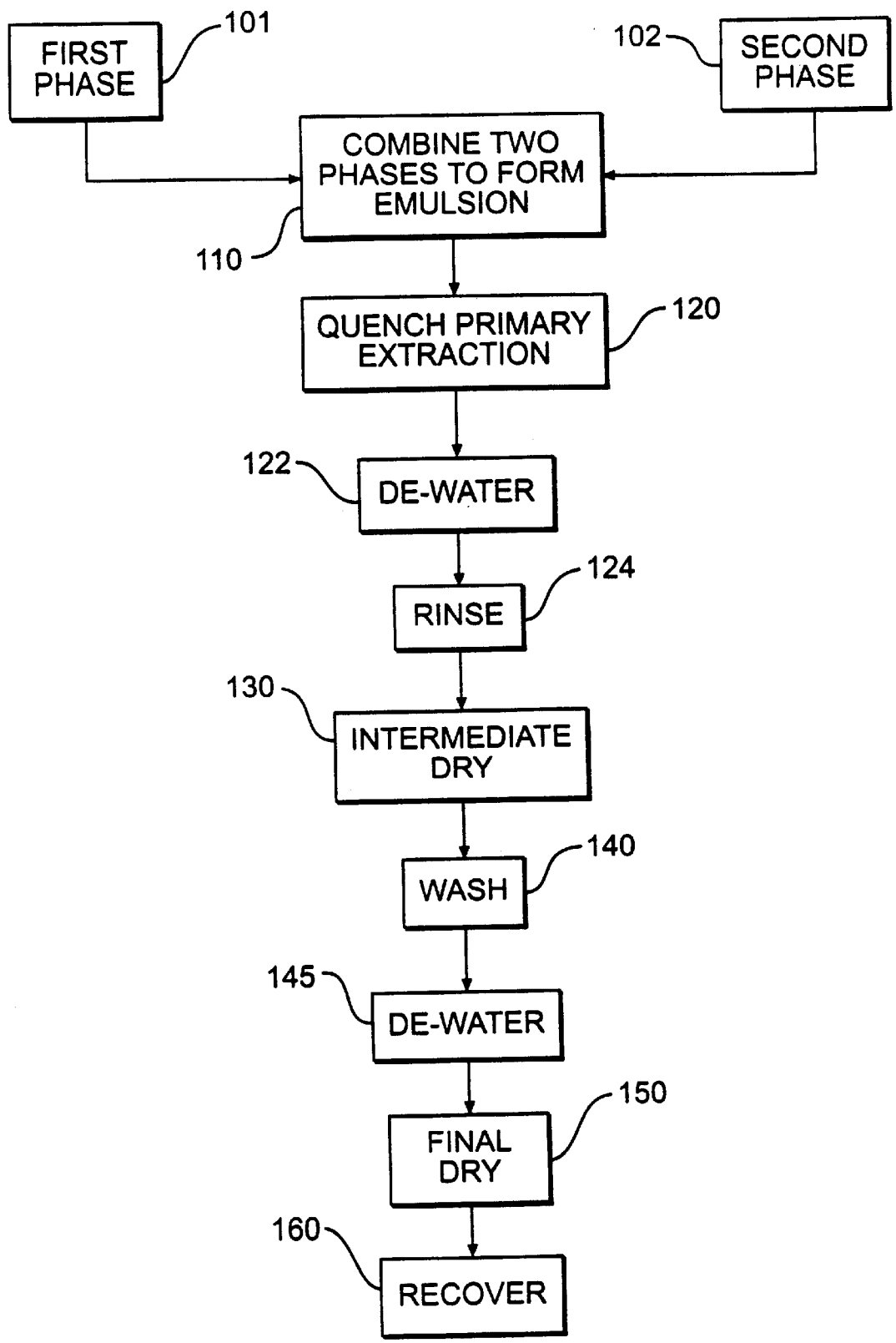
FIG. 1 shows a flow diagram illustrating one embodiment of a method for preparing microparticles in accordance with the present invention.

The present invention relates to microparticles having a selected release profile for release of the active agent from the microparticles, and to a method for the preparation of such microparticles. The release profile refers to the quantity or amount of active agent that is released from the microparticles as a function of time. Release profiles are typically illustrated as the cumulative release, expressed as a percentage of the total amount of active agent present in the microparticles, as a function of time. Different clinical applications, and/or different active agents, may require different types of release profiles. For example, one type of release profile includes an "initial burst," or release of a significant amount of active agent from the microparticles within the first 24 hour period. The initial burst may then be followed by a substantially linear release profile after the initial burst. Another type of release profile is a sigmoidal release profile. As used herein, the term "sigmoidal" refers to a release profile that is substantially "S"-shaped. As shown, for example, in FIG. 6, a sigmoidal release profile is characterized by an initial lag phase, a steep intermediate release phase, and a flat final release phase.

The inventors have unexpectedly discovered that the release profile of the microparticles can be controlled by adjusting the degree of drying that is performed on the microparticles during their preparation. Particularly, if an intermediate drying step (between the quench/primary extraction step and the washing step as explained below) is eliminated or is incomplete, then the release profile of the microparticles includes an initial burst followed by a substantially linear release profile. However, if a substantially complete intermediate drying step is performed on the microparticles, then the release profile will be substantially sigmoidal with an initial lag phase.

After the microparticles undergo the degree of intermediate drying needed for the selected release profile, the microparticles are preferably washed and subjected to a final drying step. To solve the problem of agglomeration of the microparticles during the washing step, in the process of the present invention the microparticles are first introduced into a vessel containing an extraction medium having a temperature lower than the glass transition temperature ($T_g$) of the microparticles, and the vessel is agitated to wet and to disperse the microparticles in the extraction medium. The cold extraction medium allows the microparticles to be dispersed without agglomeration caused by elevated temperatures. The microparticles are then preferably transferred to a larger extraction tank having extraction medium at a temperature higher than the glass transition temperature of the microparticles for extraction and washing.

As used herein, "glass transition temperature" or "$T_g$" refers to the temperature at which the polymer or polymer matrix material of the microparticles changes from a rigid or glassy condition to a soft rubbery condition upon heating. As would be readily apparent to one of skill in the relevant art, the $T_g$ of the microparticles will depend in part on processing conditions, such as the solvent used. For example, benzyl alcohol acts as a plasticizer that decreases the $T_g$ of the microparticles. Hydrolyzing will also decrease the $T_g$ of the microparticles. The molecular weight of the polymer also affects the $T_g$ of the microparticles—the higher the molecular weight of the polymer, the higher the $T_g$.

To ensure clarity of the description that follows, the following definitions are provided. By "initial burst" is meant release of a significant amount of active agent from the microparticles within the first 24 hour period, typically greater than about 5% cumulative release. By "microparticles" or "microspheres" is meant solid particles that contain an active agent dispersed or dissolved within a polymer that serves as the matrix of the particle. The polymer is preferably biodegradable and biocompatible. By "biodegradable" is meant a material that should degrade by bodily processes to products readily disposable by the body and should not accumulate, in the body. The products of the biodegradation should also be biocompatible with the body. By "biocompatible" is meant not toxic to the body, is pharmaceutically acceptable, is not carcinogenic, and does not significantly induce inflammation in body tissues. As used herein, "body" preferably refers to the human body, but it should be understood that body can also refer to a non-human animal body. By "weight %" or "% by weigh" is meant parts by weight per total weight of microparticle. For example, 10 wt. % active agent would mean 10 parts active agent by weight and 90 parts polymer by weight.

Method and Equipment Description

With reference now to the drawings, FIG. 1 illustrates one embodiment of a method for preparing microparticles in accordance with the present invention. In a step 110, a first phase 101 and a second phase 102 are combined to form an emulsion. One of the two phases is discontinuous, and the other of the two phases is continuous. The first phase preferably comprises an active agent, a polymer, and a solvent for the polymer.

Preferred active agents that can be encapsulated by the process of the present invention include 1,2-benzazoles, more particularly, 3-piperidinyl-substituted 1,2-benzisoxazoles and 1,2-benzisothiazoles. The most preferred active agents of this kind for treatment by the process of the present invention are 3-[2-[4-(6-fluoro1,2-benzisoxazol-3-yl)-1-piperidinyl]ethyl]-6,7,8,9-tetrahydro-2-methyl-4H-pyrido[1,2-a]pyrimidin-4-one ("risperidone") and 3-[2-[4-(6-fluro-1,2-benzisoxazol-3-yl)-1-piperidinyl] ethyl]-6,7,8,9-tetrahydro-9-hydroxy-2-methyl-4H-pyrido[1, 2-a]pyrimidin-4-one ("9-hydroxyrisperidone") and the pharmaceutically acceptable salts thereof. Risperidone (which term, as used herein, is intended to include its pharmaceutically acceptable salts) is most preferred. Risperidone can be prepared in accordance with the teachings of U.S. Pat. No. 4,804,663, the entirety of which is incorporated herein by reference. 9-hydroxyrisperidone can be prepared in accordance with the teachings of U.S. Pat. No. 5,158,952, the entirety of which is incorporated herein by reference.

Other biologically active agents that can be incorporated using the process of the present invention include gastrointestinal therapeutic agents such as aluminum hydroxide, calcium carbonate, magnesium carbonate, sodium carbonate and the like; non-steroidal antifertility agents; parasympathomimetic agents; psychotherapeutic agents; major tranquilizers such as chlorpromazine HCl, clozapine, mesoridazine, metiapine, reserpine, thioridazine and the like; minor tranquilizers such as chlordiazepoxide, diazepam meprobamate, temazepam and the like; rhinological decongestants; sedative-hynotics such as codeine, phenobarbital, sodium pentobarbital, sodium secobarbital and the like; steroids such as testosterone and tesosterone propionate; sulfonamides; sympathoomimetic agents; vaccines; vitamins and nutrients such as the essential amino acids; essential fats and the like; antimalarials such 4-aminoquinolines, 8-aminoquinolines, pyrimethaamine and the like, anti-migraine agents such as mazindol, phentermine and the like; anti-Parkinson agents such as L-dopa; anti-spasmodics such as atropine, methscopolamine bromide and the like; antispasmodics and anticholinergic agents such as bile therapy, digestants, enzymes and the like; antitussives such as dextromethorphan, noscapine and the like; bronchodilators; cardiovascular agents such as anti-hypertensive compounds, Rauwolfia alkaloids, coronary vasodilators, nitroglycerin, organic nitrates, pentaerythritotetranitrate and the like; electrolyte replacements such as potassium chloride; ergotalkaloids such as ergotamine with and without caffeine, hydrogenated ergot alkaloids, dihydroergocnstine methanesulfate, dihydroergocornine methanesulfonate, dihydroergokroypine methanesulfate and combinations thereof; alkaloids such as atropine sulfate, Belladotna, hyoscine hydrobromide and the like; analgetics, narcotics such as codeine, dihydrocodienone, meperidine, morphine and the like; nonnarcotics such as salicylates, aspirin, acetaminophen, d-propoxyphene and the like; antibiotics such as salicylates, aspirin, acetaminophen, d-propoxyphene and the like; antibiotics such as the cephalosporins, chloranphenical, gentamicin, Kanamycin A, Kanamycin B, the penicillins, ampicillin, streptomycin A, antimycin A, chloropamtheniol, metromidazole, oxytetracycline penicillin G, the tetracylines, and the like, anti-cancer agents; anticonvulsants such as mephenytoin, phenobarbital, trimethadione; anti-emetics such as thiethylperazine; antihistarnines such as chlorophinazine, dimenhydrinate, diphenhydramine, perphenazine, tripelennamine and the like; anti-inflammatory agents such as hormonal agents, hydrocortisone, prednisolone, prednisone, non-hormonal agents, allopurinol, aspirin, indomethacin, phenylbutazone and the like; prostaglandins; cytotoxic drugs such as thiotepa; chlorambucil, cyclophosphamide, melphalan, nitrogen mustard, methotrexate and the like; antigens of such microorganisms as *Neisseria gonorrhea, Mycobacterium tubercutosis*, Herpes virus (humonis, types 1 and 2), *Candida albicans, Candida tropicalis, Trichomonas vaginalis, Haemophilus vaginalis*, Group B *Streptococcus ecoli, Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis*, Equine herpes virus 1, Equine arteritis virus, IBR-IBP virus, BVD-MB virus, *Chiamydia psittaci, Trichomonasfoetus, Toxoplasma gondii Escherichia coli, Actinobacillus equuli, Salmonella abortus ovis, Salmonella aborus equi, Pseudomonas aeruginosa, Corynebacterium equi, Corynebacterium pyogenes, Actinobaccilus seminis, Mycoplasma bovigenitalium, Aspergillus fumigastus, Absidia ramosa, Trypanosoma equiperdun, Babesia caballi, Clostridium tetani*, and the like; antibodies that counteract the above microorganisms; and enzynes such as ribonucleae, neuramidinase, trypsin, glycogen phosphorylase, sperm lactic dehydrogenase, sperm hyaluronidase, adenosinetriphosphatase, alkaline phosphatase, alkaline phosphatase esterase, amino peptidase, trypsin, chymotrypsin, amnylase, muramidase, acrosomal proteinase, diesteras, glutarnic acid dehydrogenase, succinic acid dehydrogenase, betaglycophosphatase, lipase, ATP-ase alpha-peptate garniaglutamylotranspeptidase, sterol-3-beta-ol-dehydrogenase, and DPN-di-aprorasse.

Other suitable active agents include estrogens such as diethyl stilbestrol, 17-beta-estradiol, estrone, ethinyl esttadiol, mestranol, and the like; progestins such as norethindrone, norgestryl, ethynodiol diacetate, lynestrenol, medroxyprogesterone acetate, dimesthisterone, megestrol acetate, chlormadinone acetate, norgestimate, norethisterone, ethisterone, melengesirl, norethynodrel and the like; and the spermicidal compounds such as nonylphenoxypolyoxyethylene glycol, benzethonium chloride, chlorindanol and the like.

Still other suitable active agents include antifungals, antivirals, anticoagulants, anticonvulsants, antidepressants, antihistamines, hormnones, vitamins and minerals, cardiovascular agents, peptides and proteins, nucleic acids, immunological agents, antigens of such bacterial organisms as *Streptococcus pneumoniae, Haemophilus influenzae, Staphylococcus aureus, Streptococcus pyrogenes, Carynebacterium diptheriae, Bacillus anthracis, Clostnriium tetani, Clostridium botulinum, Clostridium per ingens, Streptococcus mutans, Salmonella lyphi, Haemophilus parainfluenzae, Bordetella pertussis, Francisella tularensis, Yersinia pestis, Vibrio cholerae, Legionella pneumophila, Mycobacteium leprae, Leptspirosis interrogans, Borrelia burgdorferi, Campylobacter jejuni*, antigens of such viruses as smallpox, influenza A and B, respiratory syncytial, parainfluenza, measles, HWV, varicella-zoster, herpes simplex 1 and 2, cytomeglavirus, Epstein-Barr, rotavirus, rhinovirus, adenovirus, papillomavirus, poliovirus. mumps, rabies, rubella, coxsackieviruses, equine encephalitis, Japanese encephalitis, yellow fever, Rift Valley fever, lymphocytic choriomeningitis, hepatitis B, antigens of such fungal protozoan, and parasitic organisms such as *Cryptococcuc neofonnans, Histoplasma capsulatwn, Candida albicans, Candida tropicalis, Nocardia asteroides, Rickettsia ricketsii, Rickettsia typh, Mycoplasma pnewnoniae, Chlamydial psittaci Chamydial trachomatis, Plmodiumfalcipatunm Trypanosoma brucei, Entamoeba histolytica, Taxoplasma gondii, Trichomonas vaginalis, Schistosonm nmnsoni*. These antigens may be in the form of whole killed organisms, peptides, proteins, glycoproteins, carbohydrates, or combinations thereof.

Still other macromolecular bioactive agents that may be chosen for incorporation include, but are not limited to, blood clotting factors, hemopoietic factors, cytokines, interleukins, colony stimulating factors, growth factors, and analogs and fragments thereof.

The microparticles can be mixed by size or by type so as to provide for the delivery of active agent to the patient in a multiphasic manner and/or in a manner that provides different active agents to the patient at different times, or a mixture of active agents at the same time. For example, secondary antibiotics, vaccines, or any desired active agent, either in microparticle form or in conventional, unencapsulated form can be blended with a primary active agent and provided to the patient.

Preferred examples of polymer matrix materials include poly(glycolic acid), poly(d,l-lactic acid), poly(l-lactic acid), copolymers of the foregoing, and the like. Various commercially available poly(lactide-co-glycolide) materials (PLGA) may be used in the method of the present invention. For example, poly (d,l-lactic-co-glycolic acid) is commercially available from Alkermes, Inc. (Blue Ash, Ohio.). A suitable product commercially available from Alkermes, Inc. is a 50:50 poly(d,l-lactic-co-glycolic acid) known as MEDISORB® 5050 DL. This product has a mole percent composition of 50% lactide and 50% glycolide. Other suitable commercially available products are MEDISORB® 6535 DL, 7525 DL, 8515 DL and poly(d,l-lactic acid) (100 DL). Poly(lactide-co-glycolides) are also commercially available from Boehringer Ingelheim (Germany) under its Resomer® mark, e.g., PLGA 50:50 (Resomer® RG 502), PLGA 75:25 (Resomer® RG 752) and d,l-PLA (Resomer® RG 206), and from Birmingham Polymers (Birmingham, Ala.). These copolymers are available in a wide range of molecular weights and ratios of lactic acid to glycolic acid.

The most preferred polymer for use in the practice of the invention is the copolymer, poly(d,l-lactide-co-glycolide). It is preferred that the molar ratio of lactide to glycolide in such a copolymer be in the range of from about 85:15 to about 50:50.

The molecular weight of the polymeric matrix material is of some importance. The molecular weight should be high enough to permit the formation of satisfactory polymer coating, i.e., the polymer should be a good film former. Usually, a satisfactory molecular weight is in the range of 5,000 to 500,000 daltons, preferably about 150,000 daltons. However, since the properties of the film are also partially dependent on the particular polymeric matrix material being used, it is very difficult to specify an appropriate molecular weight range for all polymers. The molecular weight of the polymer is also important from the point of view of its influence upon the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microparticle formulation can be made in which the resulting microparticles exhibit both diffusional release and biodegradation release properties. This is useful in according multiphasic release patterns.

The formulation prepared by the process of the present invention contains an active agent dispersed in the microparticle polymeric matrix material. The amount of such agent incorporated in the microparticles usually ranges from about 1 wt. % to about 90 wt. %, preferably 30 to 50 wt. %, more preferably 35 to 40 wt. %.

The emulsion is transferred into a quench liquid for the quench or primary extraction step (120). The primary purpose of the quench step is to extract or remove residual solvent from the microparticles that are formed. In a preferred embodiment of the present invention, quench step 120 is followed by a de-watering step 122 and a rinse step 124. The objective of de-watering step 122 is to concentrate the microparticles from the dilute suspension that is formed during extraction step 120 to a concentrated slurry prior to subsequent drying of the microparticies. The objective of rinse step 124 is to reduce stickiness of the microparticles. Alternatively, rinse step 124 is omitted so that drying occurs after de-watering step 122.

An intermediate drying step 130 is performed after rinse step 124, or, alternatively, after de-watering step 122 if the rinse step is omitted. The objective of intermediate drying step 130 is to perform a degree of intermediate drying of the microparticles so that the selected release profile is achieved. As will be explained in more detail below in the Examples, when the degree of intermediate drying performed in step 130 is no intermediate drying, the result is microparticles having an initial burst and a substantially linear release profile. When the degree of intermediate drying performed in step 130 is substantially complete intermediate drying, the result is microparticles having an initial lag phase and a substantially sigmoidal release profile.

After intermediate drying step 130, the micropartcles are washed in a step 140 to remove or extract any further residual solvent. The microparticles are de-watered in a step 145 prior to a final drying step 150. Final drying step 150 is preferably carried out so that the moisture content of the microparticles is less than about 1%, more preferably approximately equal to about 0.2%. The microparticles are recovered in a step 160.

Figure 2:
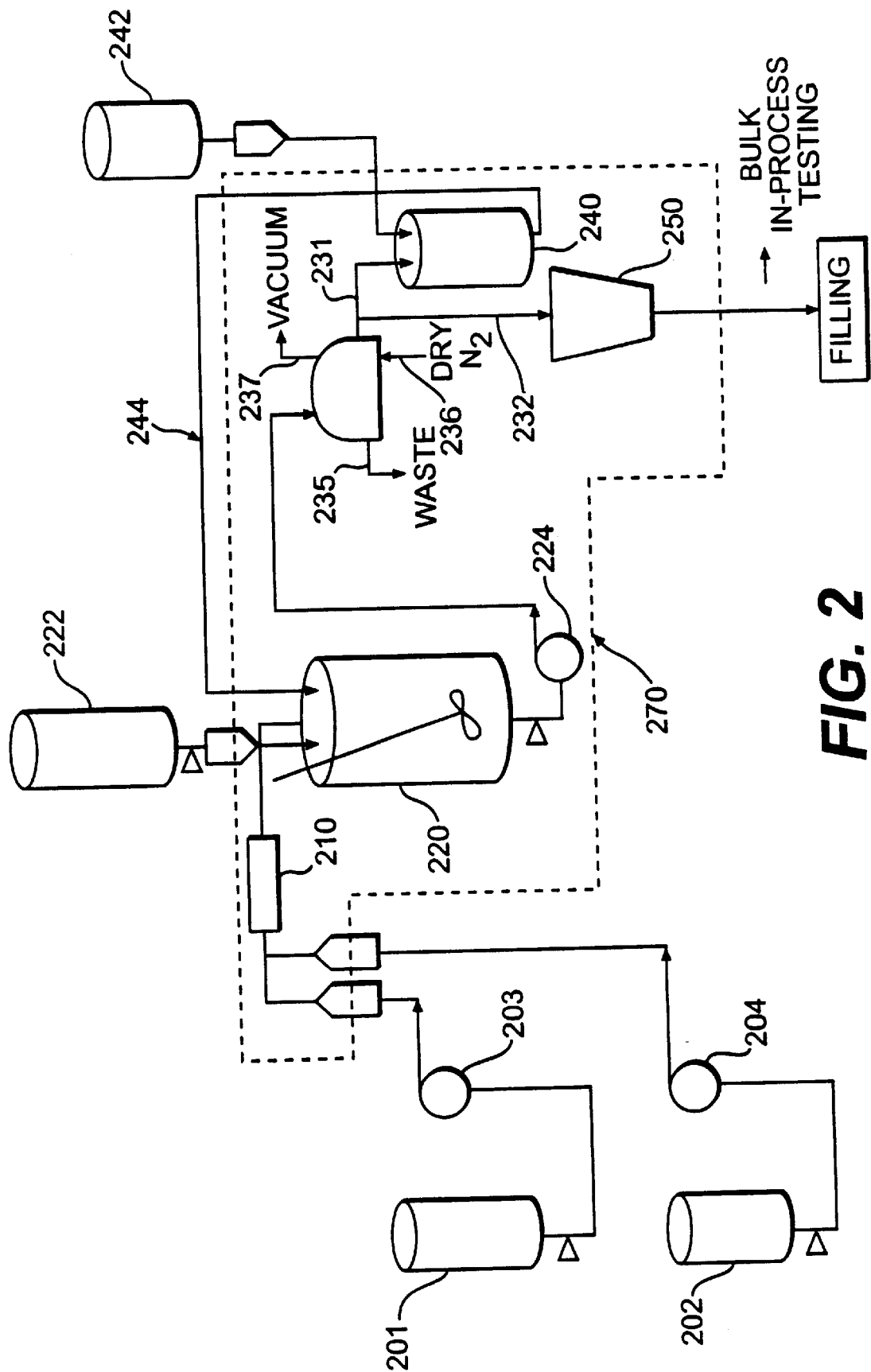
FIG. 2 shows one embodiment of an equipment configuration for preparing microparticles in accordance with the present invention, the embodiment shown in FIG. 2 suitable for performing a degree of intermediate drying ranging from no intermediate drying to substantially complete intermediate drying.

With reference now to FIG. 2, one embodiment is shown of an equipment configuration for preparing microparticles in accordance with the present invention. The embodiment shown in FIG. 2 is particularly well suited for performing a degree of intermediate drying ranging from no intermediate drying to substantially complete intermediate drying. In a preferred embodiment of the present invention, the equipment contained within the dotted line boundary shown generally at 270 is sterilized using a "steam-in-place" (SIP) process.

A first phase 201 is provided. First phase 201 is preferably the discontinuous phase, comprising a polymer dissolved in one or more solvents, and an active agent. The active agent can be dissolved or dispersed in the same or a different solvent than the solvent(s) in which the polymer is dissolved. A second phase 202 is preferably the continuous phase, preferably comprising water as the continuous processing medium. Preferably, an emulsifying agent such as a surfactant or a hydrophilic colloid is added to the continuous phase to prevent the microdroplets from agglomerating and to control the size of the mincrodroplets in the emulsion. Examples of compounds that can be used as surfactants or hydrophilic colloids include, but are not limited to, poly (vinyl alcohol) (PVA), carboxymethyl cellulose, gelatin, poly(vinyl. pyrrolidone), Tween 80, Tween 20, and the like. The concentration of surfactant or hydrophilic colloid in the continuous phase will be from about 0.1% to about 10% by weight based on the continuous processing medium, depending upon the surfactant; hydrophilic colloidc, the discontinuous phase, and the continuous processing medium used. A preferred continuous phase is 0.1 to 10 wt. %, more preferably 0.5 to 2 wt. %, solution of PVA in water. Although not absolutely necessary, it is preferred to saturate the continuous phase with at least one of the solvents forming the discontinuous phase. This provides a stable emulsion, preventing transport of solvent out of the microparticles prior to quench step 120.

First phase 201 and second phase 202 are combined under the influence of mixing means to form an emulsion. A preferred type of mixing means is a static mixer 210. Other mixing lmeans suitable for use with the present invention include, but are not limited to, devices for mechanically agitating the first and second phases, such as homogenizers, propellers, impellers, stirrers, and the like.

Preferably, the discontinuous and continuous phases 201 and 202 are pumped through static mixer 210 to form an emulsion, and into a large volume of quench liquid, to obtain microparticles containing the active agent encapsulated in the polymeric matrix material. A pump 203 pumps first phase 201 into static mixer 210, and a pump 204 pumps second phase 202 into static mixer 210. An especially preferred method of mixing with a static mixer in the process of the present invention is disclosed in U.S. Pat. No. 5,654,008, the entirety of which is incorporated herein by reference.

First and second phases 201 and 202 are mixed in static mixer 210 to form an emulsion. The emulsion formed comprises microparticles containing active agent encapsulated in the polymeric matrix material. The niucroparticles are then preferably stirred in Ach or extraction tank 220 containing a quench liquid in order to remove most of the solvent from the microparticles, resulting in the formation of hardened microparticles. Following the moveiment of the microparticles from static mixer 210 and entrance into quench tank 220, the continuous processing medium is diluted, and much of the solvent in the microparticles is removed by extraction. In this extractive queench step (120), the microparticles can be suspended in the same continuous phase (second phase 202) used during emulsification, with or without hydrophilic colloid or surfactant, or in another quench liquid. The quench liquid removes a significant portion of the solvent from the microparticles, but does not dissolve them. During the extractive quench step, the quench liquid containing dissolved solvent can, optionally, be removed and replaced with fresh quench liquid.

Upon completion of quench step 120 in quench tank 220, the microparticles are transferred by a pump 224 to a device 230 that functions as a microparticle collecting device, de-watering device, and drying device. Device 230 is used to carry out de-watering step 122, rinse step 124, intermediate drying step 130, de-watering step 145, and final drying step 150.

Device 230 comprises a vibrating sieve or screen. The vibration causes smaller particles and liquid to drop through the screen, while larger particles are retained. The smaller particles and liquid that drop through the screen are removed as waste 235. Device 230 also functions as a vacuum dryer, through the use of a vacuum line 237. The microparticles are fluidized by the vibrational energy, and by a small amount of a dry gas bleed, preferably a dry nitrogen ($N_2$) bleed 236. The dry nitrogen bleed, passed on the underside of the screen, helps the microparticles dry more quickly and without agglomeration by assisting in keeping the microparticles moving around. After drying, an internal port on the screen may be opened, and the vibrational energy causes the remaining microparticles to self-discharge.

A suitable device 230 for a process of approximately 1 Kg scale is a PHARMASEP Model PH12Y vibratory sieve available from Sweco, Florence, Kentucky. This device consists of a 25μ (nom) stainless steel screen approximately eleven inches in diameter that fits in a stainless steel frame. The frame is attached to a base weldment. A smaller six-inch diameter 150 μ screen may also be attached to the weldment but positioned upstream from the 25μ screen to filter out oversized material. The machine is driven by a one-third horsepower motor (motion generator) designed to transmit vibration to the screen(s).

After the completion of intermediate drying step 130, the dried microparticles need to be transferred to another extraction medium to carry out wash step 140. Wash step 140 is preferably carried out in quench tank 220, using an extraction medium 222 having a temperature higher than the glass transition temperature ($T_g$) of the microparticles. Directly dispersing the dried microparticles (now in the form of a dry powder) in quench tank 220 is problematic because the dry powder takes time to wet out before dispersing. Because the temperature of the extraction medium in quench tank 220 is higher than the microparticle $T_g$, the microparticles have a tendency to agglomerate before dispersing. The process of the present invention solves this agglomeration problem in the following manner. To carry out wash step 140, the micropaticles are first introduced into a re-slurry tank or other type of vessel 240, as shown by path 231. The temperature of the extraction medium 242 that is used in vessel 240 is lower than the $T_g$ of the microparticles. The cold extraction medium in vessel 240 allows the dried microparticles to wet and to disperse without agglomeration caused by elevated temperatures, i.e., temperatures aboWe the $T_g$ of the microparticies.

At the time of transfer of the microparticles into extraction medium 222 in quench tank 220, the temperature of extraction medium 222 is higher than the $T_g$ of the microparticles. The $T_g$ of the microparticles changes during wash step 140 as solvents are extracted. At the end of wash step 140, the $T_g$ of the rnicroparticles is higher than the temperature of extraction medium 222.

Vessel 240 is preferably smaller in size/volume than quench tank 220; consequently the volume of extraction medium in vessel 240 will be less than the volume of extraction medium in quench tank 220. The volume of the extraction medium in vessel 240 is preferably small enough relative to the volume of extraction medium in quench tank 220 so that when the extraction medium and microparticles are transferred from vessel 240 into quench tank 220 (as shown by path 244), the temperature of the extraction medium in quench tank 220 is affected only a few degrees.

Vessel 240 preferably has an impeller or other form of agitating device used to agitate the vessel contents, but preferably does not include any baffles. The smaller volume of vessel 240 allows intense agitation so that the microparticles can be dispersed in the extraction medium.

After wash step 140 is completed in quench tank 220, the microparticles are again transferred via pump 224 into device 230 for de-watering step 145 and final drying step 150. At the completion of final drying step 150, the microparticles are discharged from device 230 in the manner described above into a sifter 250, as shown by path 232. Sifter 250 is used to fractionate the microp articles by size for filling into vials and for bulk in-process testing (e.g., aspect, active agent content, residual solvents, in vitro release, and particle size distribution).

Figure 3:
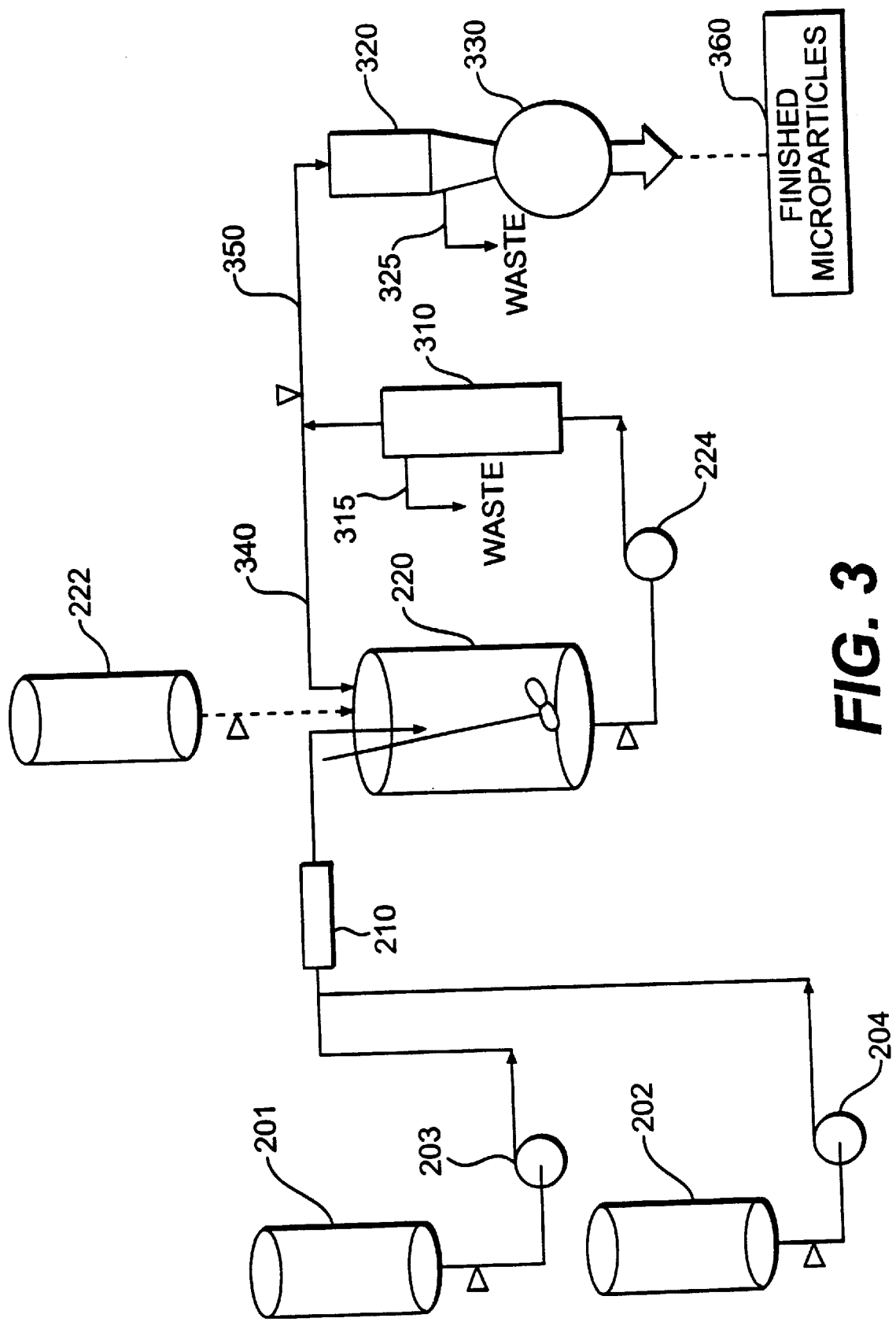
FIG. 3 shows another embodiment of an equipment configuration for preparing microparticles in accordance with the present invention, the embodiment shown in FIG. 3 suitable for performing no intermediate drying.

FIG. 3 shows another embodiment of an equipment configuration for preparing microparticles in accordance with the present invention. The embodiment shown in FIG. 3 is particularly suitable for performing no intermediate drying. As with the embodiment shown in FIG. 2, the embodiment of FIG. 3 combines first and second phases 201 and 202 in static mixer 210 to form an emulsion. Quench step 120 is carried out in quench tank 220.

Upon completion of quench step 120, the microparticles are transferred via pump 224 through a filter 310 that removes small particles and excess liquid through a waste line 315. The microparticles are then transferred back into quench tank 220 along path 340 to perform wash step 140 using extraction medium 222. In this embodiment, intermediate drying step 130 is effectively eliminated, i.e., a degree of intermediate drying that is no intermediate drying.

Upon completion of wash step 140, the microparticles are transferred via pump 224 through filter 310 along path 350 into a strainer 320 for de-watering step 145. Excess water and waste is removed from strainer 320 via a waste line 325. Final drying step 150 is performed in a dryer 330, from which finished microparticles 360 are recovered.

Figure 4:
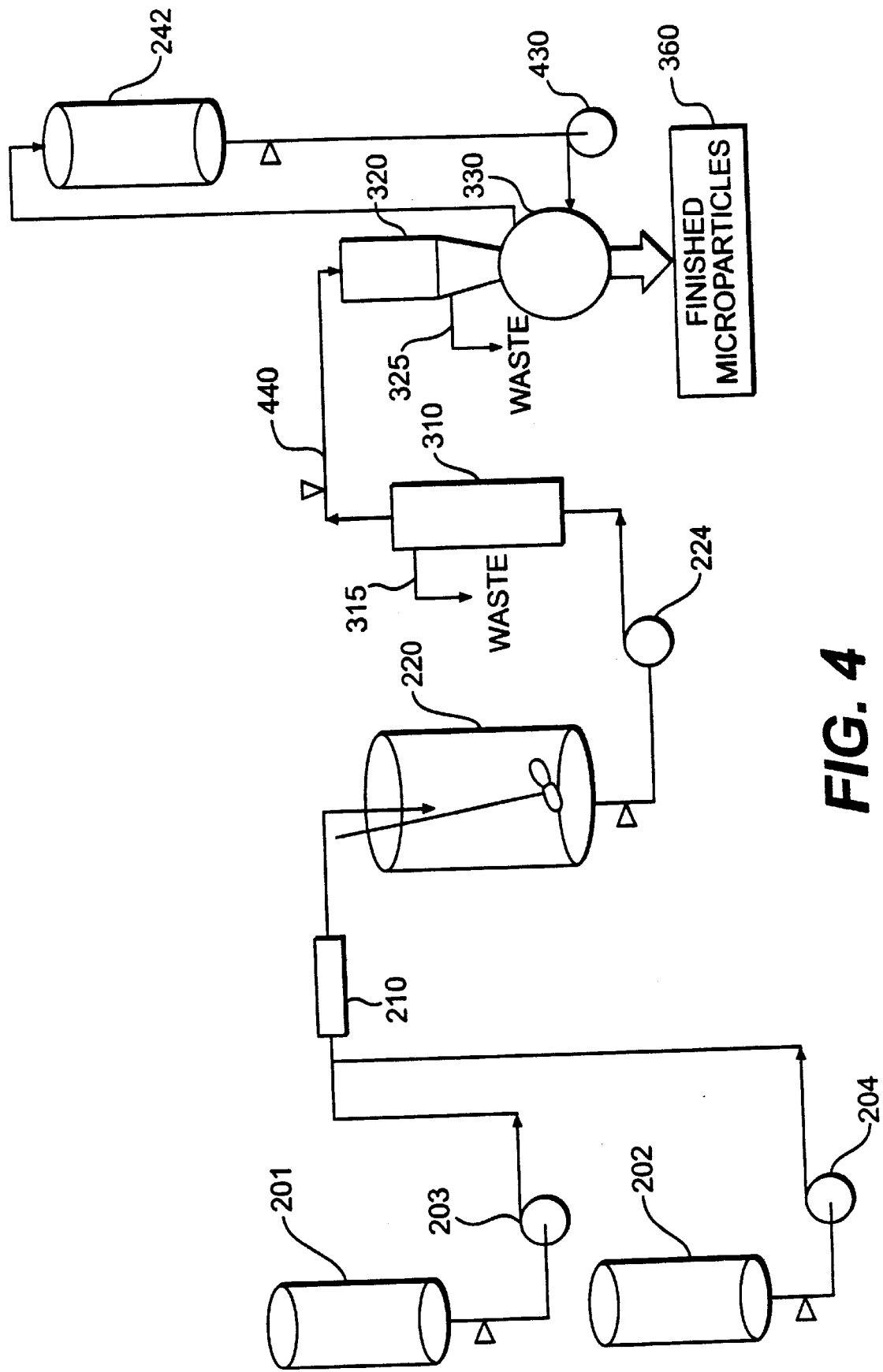
FIG. 4 shows yet another embodiment of an equipment configuration for preparing microparticles in accordance with the present invention, the embodiment shown in FIG. 4 suitable for performing no intermediate drying with washing in the dryer.

FIG. 4 shows an alternate embodiment of an equipment configuration suitable for performing no intermediate drying. In the embodiment shown in FIG. 4, intermediate drying step 130 is effectively eliminated, i.e., a degree of intermediate drying that is no intermediate drying, and wash step 140 is performed in dryer 330.

As with the embodiments shown in FIGS. 2 and 3, the embodiment of FIG. 4 combines first and second phases 201 and 202 in static mixer 210 to form an emulsion. Quench step 120 is carried out in quench tank 220.

Upon completion of quench step 120, the microparticles are transferred via pump 224 through filter 310 that removes small particles and excess liquid through waste line 315. The microparticles are then transferred along path 440 through strainer 320 and into dryer 330. Extraction medium 242 is transferred into dryer 330 via pump 430 so that wash step 140 can be performed in dryer 330.

De-watering step 145 and final drying step 150 become essentially the same step using the embodiment of FIG. 4. The final drying is performed in dryer 330, from which finished microparticles 360 are recovered.

EXAMPLES

The following examples further describe the materials and methods used in carrying out the invention. The examples are not intended to limit the invention in any manner.

Example 1

Effect of Drying Parameters on In Vitro Release

Nine samples were prepared in accordance with the 1 Kg process described below in Example 6. Intermediate drying step 130 was varied to determine the effect on the 24 hour in vitro release. An example of measurement of in vitro release is provided below in Example: 7. As shown below in Table 1, the intermediate drying step varied from no intermediate drying (sample K), to drying under vacuum in a dryer (samples L, M, and N), to drying under vacuum in a dryer with an additional dry gas sweep (samples O, P, Q, R, and 0121-7). The highest 24 hour in vitro release occurred for the samples having the least amount of intermediate drying. Conversely, the lowest 24 hour in vitro release occurred for the samples having the greater amount of intermediate drying. It was found that substantially complete intermediate drying was achieved by drying under vacuum for a period in the range of approximately 18–24 hours, and drying with a gas sweep (such as a $N_2$ or an air sweep) for a period in the range of approximately 6–24 hours.

TABLE 1

Effect of drying parameters on in vitro burst

| Sample 0121-7- | Initial time in dryer hrs | Addl. dry gas sweep hrs | 24 hr in vitro release % |
|---|---|---|---|
| K | 0 | 0 | 12.6 |
| L | 6 | 0 | 16.1 |
| M | 12 | 0 | 16.8 |
| N | 18 | 0 | 5.3 |
| O | 18 | 6 | 4.3 |
| P | 18 | 12 | 8.3 |
| Q | 18 | 18 | 2.7 |
| R | 18 | 24 | 3.3 |
| 0121-7 | 18 | 24 | 3.4 |

Example 2

Effect of Drying Parameters on 15-Day Release

Nine sample were prepared in accordance with the 1 Kg process described below, in Example 6. As shown below in Table 2, for six of the samples, intermediate drying step 130 was performed to achieve substantially complete intermediate drying using vacuum drying with an air sweep. For two of the samples, intermediate drying step 130 was performed as no intermediate drying. For one sample, intermediate drying step 130 was performed to be a degree of intermediate drying that is partial intermediate drying, between no intermediate drying o:and substantially comple intermediate drying.

As shown in Table 2, the in vitro release at 15 days was highest for the samples for which no intermediate drying was performed. The samples for which substantially complete intermediate drying was performed showed a cumulative release of active agent from the microparticles than about 15% after 15 days. The sample for which partial intermediate drying was performed had a 15 day release between the substantially complete intermediate drying samples and the no intermediate drying samples.

TABLE 2

Effect of drying parameters on 15-day release

| Sample | Amount of drying (with air sweep) | % Released @ 15 days |
|---|---|---|
| 715 | Complete | 13.6 |
| 903 | Complete | 9.4 |
| 909 | Complete | 12.6 |
| 1015 | Complete | 7.8 |
| 1216 | Complete | 10.2 |
| 0107 | Complete | 6.7 |
| 813 | None | 30.5 |
| 826 | None | 32.1 |
| 916 | Partial | 19.3 |

Example 3

Moisture Data and Drying Time

Four batches (0812-7, 0819-7, 0825-7, and 0902-7) were prepared in accordance with the 1 Kg process described below. Table 3 below shows the time in hours of intermediate drying step 130, performed using a small dry $N_2$ bleed under a full vacuum. The percent moisture was measured using a batch sample after the indicated drying time using a Karl Fischer process (U.S. Pharmacopeia 921) known to one of skill in the relevant art For samples 0819-7a and 0902-7g, the percent release was measured after 24 hours and after 15 days. These samples exhibit minimal release within 24 hours, indicative of an initial lag phase in release of the active agent. The cumulative release of active agent from these samples are 10.3% and 8.3%, respectively, after 15 days. Samples 0812-7a, 7b, 7c, 0819-7a, 0825-7a, and 0902-7g represent substantially complete intermediate drying, resulting in a moisture content of less than about 0.2% after intermediate drying. Samples 0902-7e and 7f represent a degree of intermediate drying between substantially complete intermediate drying and no intermediate drying, resulting in a moisture content of approximately 7% after intermediate drying.

TABLE 3

| Sample # | Time Hrs. | Moisture % | 24 Hours Cumulative Release % | 15 days Cumulative Release % |
|---|---|---|---|---|
| -0812-7a | 16.26 | 0.14 | | |
| -0812-7b | 23 | 0.10 | | |
| -0812-7c | 40 | 0.08 | | |
| -0819-7a | 16.5 | 0.11 | 1.3 | 10.3 |
| -0825-7a | 40.6 | 0.10 | | |
| -0902-7e | 7.25 | 6.78 | | |
| -0902-7f | 7.25 | 6.99 | | |
| -0902-7g | 23 | 0.09 | 1.0 | 8.3 |

Example 4

In Vitro Release Profiles

Figure 5:
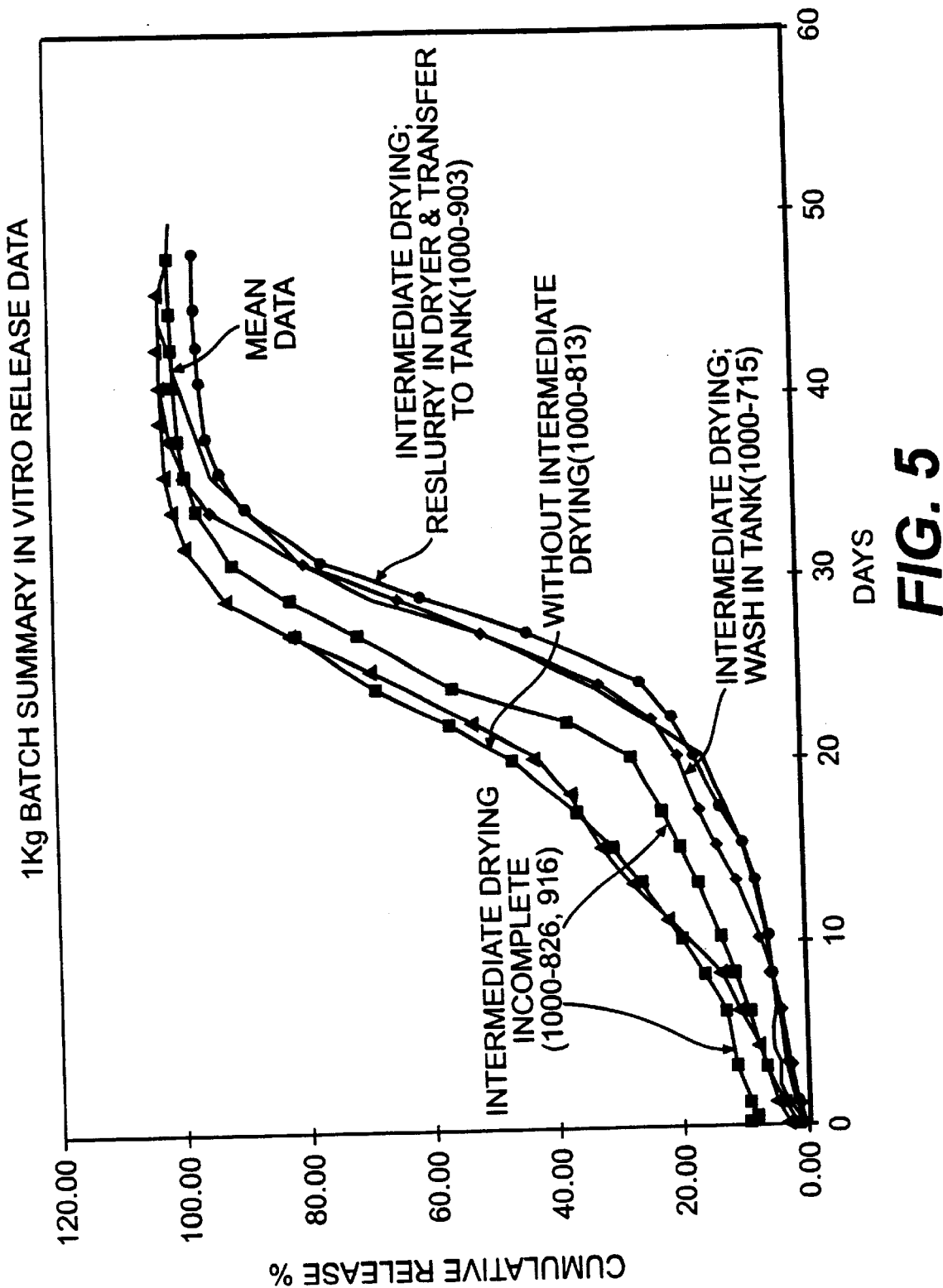
FIG. 5 shows a graph of in vitro release profiles (Cumulative Release %) as a function of time to illustrate the effect of the degree of intermediate drying on in vitro release.

The in vitro release profiles shown in FIG. 5 illustrate the effect on release profiles as a function of the degree of intermediate drying. The solid line without any data points labeled "Mean Data" represents a baseline sigmoidal release profile. The line labeled "Without Intermediate Drying" (▼ shaped data points), and the two lines labeled "Intermediate Drying Incomplete" (two lines with ■ shaped data points), have a higher release within 24 hours than does the Mean Data line, and these three lines are more linear and less "S"-shaped than the Mean Data Line.

In contrast, the two lines labeled "Intermediate Drying" (▼ and ─ shaped data points), have a low release within 24 hours like the Mean Data line, and an "S"-shaped sigmoidal release profile that closely follows the Mean Data line.

Example 5

Sigmoidal Release Profiles

Figure 6:
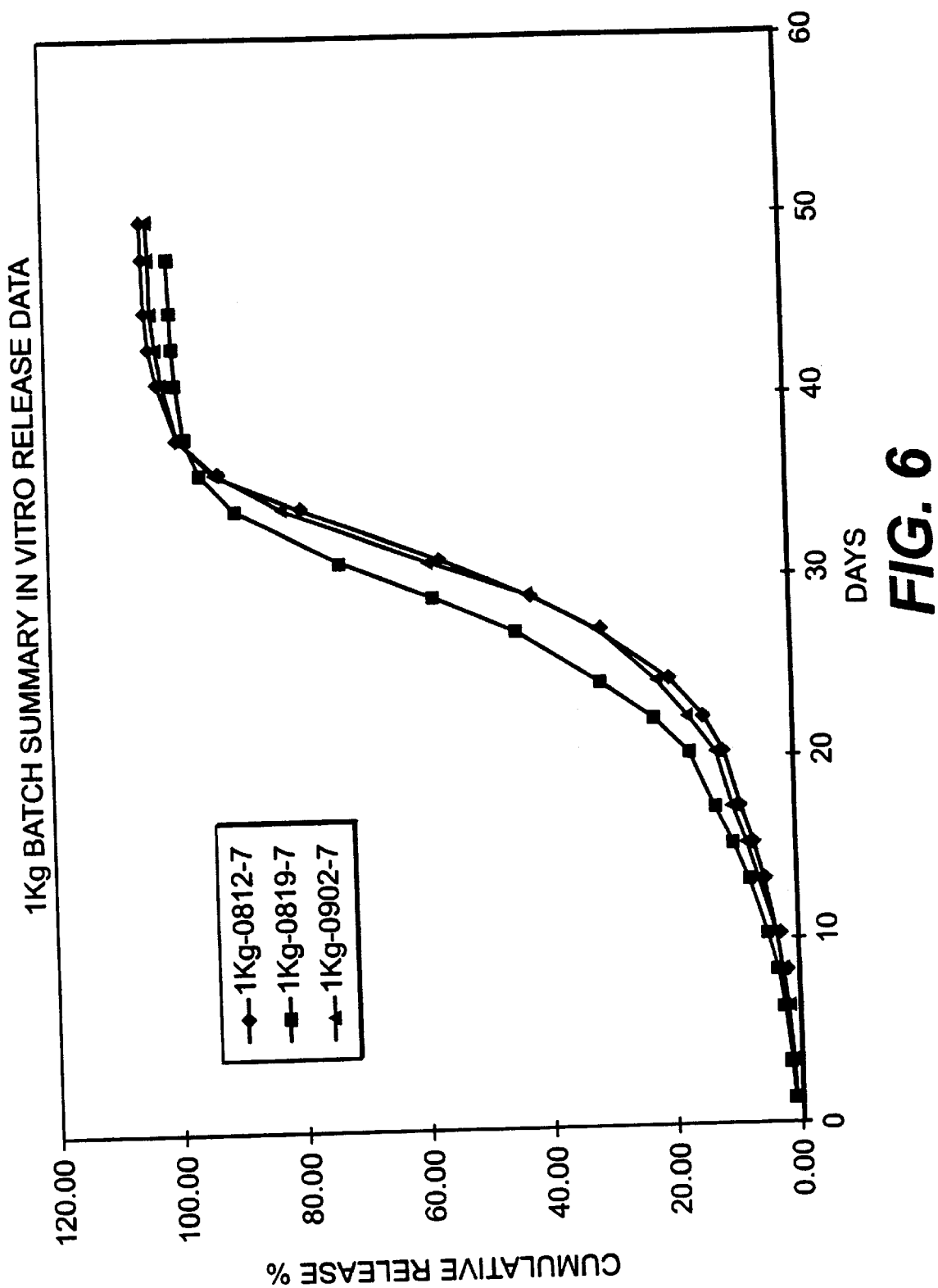
FIG. 6 shows a graph of cumulative release profiles (Cumulative Release %) as a function of time of microparticles made with substantially complete intermediate drying to achieve a sigmoidal release profile.

FIG. 6 shows the release profiles for three batches (0812-7, 0819-7, and 0902-7) that were prepared in accordance with the 1 Kg process described below in Example 6. Each release profile shown in FIG. 6 is a sigmoidal release profile characterized by an initial lag phase (approximately days 1–15), a steep intermediate release phase (approximately days 16–40), and a flat final release phase (approximately days 41–60). Each batch was divided into three sub-samples for in vitro release measurements. The average cumulative release (%) of the three sub samples after day 1 (24 hours) was 0.97% for batch 0812-7, 1.03% for batch 0902-7, and 1.33% for batch 0819-7. The average cumulative release (%) of the three sub-samples after day 15 was 7.36% for batch 0812-7, 8.33% for batch 0902-7, and 10.34% for batch 0819-7. Thus, these samples prepared with substantially complete intermediate drying exhibit minimal release within 24 hours, with an initial lag phase in release of the active agent. Further, the cumulative release of active agent from the microparticles was less than about 15% after 15 days.

Example 6

1 Kg Process

A process for preparing microparticles containing risperidone as the active agent in accordance with the present invention will now be described. The following 1 Kg process (400 grams of active agent and 600 grams of polymer) is preferably carried out using the equipment configuration shown in FIG. 2. The theoretical drug loading of the microparticles is 40%. The actual drug loading that is achieved by the process described below ranges from about 35%, to about 39%.

A drug solution is prepared by dissolving 400 grams of risperidone (Janssen Pharmaceutica, Beerse, Belgium) in 1267 grams of benzyl alcohol to form a 24 wt. % drag solution. A polymer solution is formed by dissolving 600 grams of 75:25 DL PLGA polymer (Alkermes, Inc., Blue Ash, Ohio) in 3000 grams of ethyl acetate to form a 16.7 wt. % polymer solution. The drug solution and the polymer solution are combined to form a first, discontinuous phase.

The second, continuous phase is prepared by preparing a 30 liter solution of 1% PVA,. the PVA acting as an emulsifier. To this is added 2086 grams of ethyl acetate to form a 6.5 wt. % solution of ethyl acetate.

The two phases are combined using a static mixer, such as a ½" Kenics static mixer available from Chemineer, Inc., North Andover, Mass. A total flow rate of 3 L/min generally provides microparticle size distributions with a mass median diameter (MD) in the range of about 80–90µ. The ratio of continuous phase to discontinuous phase is 5:1 (v/v). The length of the static mixer can vary from about 9 inches to about 88 inches. Lengths greater than about 48 inches results in the greatest percent yield in a microparticle size range of 25–150µ.

The quench liquid is 2.5% solution of ethyl acetate and water-for-injection (WFD at 5–10° C. The volume of the quench liquid is 0.25L per gram of batch size. The quench step is carried out for a time period greater than about 4 hours, with stirring of the microparticles in the quench tank.

After completion of the quench step, the microparticles are transferred to the collecting, de-watering, and drying device 230 shown in FIG. 2 and described above. The microparticles are rinsed using a chilled (approximately 5° C.) 17 liter 25% ethanol solution.

To form microparticles with a sigmoidal release profile, the microparticles are then subjected to substantially complete intermediate drying. The microparticles are dried in device 230 using vacuum and a 2–26 SCFH (Standard Cubic Feet per Hour) of nitrogen bleed. To avoid agglomeration, the temperature is maintained at less than 10° C. by chilling the feed nitrogen. Dryness is monitored by an absolute humidity probe, available from Vaisala, Inc., Woburn, Mass., in the vacuum line of the drying device. Absolute humidity refers to the ratio of the mass of water vapor to the volume of moist air within which the water vapor is contained. To ensure a sigmoidal release profile with an initial lag phase, the drying is carried for a time period greater than about four hours after substantially zero absolute humidity is reached in the drying device. The moisture content of the microparticles at this point is typically less than about 0.2%, generally less than about 0.15%. If the microparticles are not substantially completely dried at this point, then the release profile will be altered to eliminate the lag phase, resulting in an initial burst followed by a substantially linear release profile. The substantially complete intermediate drying can be performed by drying under vacuum with a gas bleed or sweep (air, nitrogen or other dry gas) for a period in the range of approximately 16–48 hours.

The microparticles are then re-slurried in a re-slurry tank (such as vessel 240 shown in FIG. 2) using a 25% ethanol solution (extraction medium) maintained at a temperature lower than the $T_g$ of the microparticles. The temperature in the re-slurry tank is preferably in the range of about 0° C. to about 15° C., preferably less than about 10° C., still more preferably 6°±2° C. The microparticles are then transferred back to the quench tank for washing for a time period of at least 6 hours with another extraction medium (25% ethanol solution) that is maintained at a temperature higher than the $T_g$ of the microparticles. The $T_g$ of the microparticles is about 18° C. (about room temperature), and the temperature of the extraction medium in the quench tank is greater than about 18° C., preferably 25°±1° C.

The microparticles are transferred back to the collecting, de-watering, and drying device for de-watering and final drying. The final drying step is carried out in a manner similar to that described above for the intermediate drying step, but the temperature is warmed to greater than about 20° C. but below 40° C. Drying continues for a time period greater than about 16 hours.

Example 7

Measurement of In Vitro Release

To measure in vitro release as a function of time for a sample of microparticles, the sample is incubated in physiological (pH7) buffer at 37° C. At periodic time points, a test sample of the incubating sample is drawn. Release of the active agent into the buffer in the test sample is measured spectrophotometrically in a manner well known to one of skill in the relevant art. The results are typically presented as cumulative release % as a function of time.

Conclusion

While various embodiments of the present invention have been described above, it should be understood that they have been presented by way of example only, and not limitation. The present invention is not limited to a particular active agent, polymer or solvent, nor is the present invention limited to a particular scale or batch size. Thus, the breadth and scope of the present invention should not be limited by any of the above-described exemplary embodiments, but should be defined only in accordance with the following claims and their equivalents.

What is claimed is:

1. A method for preparing microparticles having a selected release profile for release of active agent contained in the microparticles, comprising:
    (a) preparing an emulsion that comprises a first phase and a second phase, wherein the first phase comprises the active agent, a polymer, and a solvent for the polymer;
    (b) extracting at least a portion of the solvent from the emulsion to form microparticles containing the active agent;
    (c) selecting a degree of intermediate drying of the microparticles to be performed so that the selected release profile is achieved; and
    (d) final drying the microparticles.

2. The method of claim 1, wherein the selecting step (c) is carried out to select no intermediate drying, thereby resulting in microparticles having an initial burst and a substantially linear release profile.

3. The method of claim 1, wherein the selecting step (c) is carried out to select substantially complete intermediate drying, thereby resulting in microparticles having an initial lag phase and a substantially sigmoidal release profile.

4. The method of claim 3, further comprising after step (c):
    (e) performing the selected degree of intermediate drying.

5. The method of claim 4, wherein the substantially complete intermediate drying results in the microparticles having a moisture content of less than about 0.2% after step (e).

6. The method of claim 1, further comprising after step (c):
    (e) washing the microparticles.

7. The method of claim 1, wherein extracting step (b) is carried out using a quench liquid.

8. A method for controlling a release profile of an active agent contained in microparticles, comprising:
    (a) forming microparticles containing the active agent;
    (b) selecting a degree of drying of the microparticles to be performed, wherein the degree of drying affects the release profile of the active agent from the microparticles; and
    (c) performing the selected degree of drying.

9. The method of claim 8, wherein the selecting step (b) is carried out to select final drying and no intermediate drying, thereby resulting in an initial burst of the active agent and a substantially linear release of the active agent.

10. The method of claim 8, wherein the selecting step (b) is carried out to select final drying and substantially complete intermediate drying, thereby resulting in an initial lag in release of the active agent, and a substantially sigmoidal release of the active agent.

11. A microencapsulated active agent having a selected release profile prepared by a method for preparing microparticles, the method comprising:
    (a) preparing an emulsion that comprises a first phase and a second phase, wherein the first phase comprises the active agent, a polymer, and a solvent for the polymer;
    (b) extracting at least a portion of the solvent from the emulsion to form microparticles containing the active agent;
    (c) selecting a degree of intermediate drying of the microparticles to be performed so that the selected release profile is achieved; and
    (d) final drying the microparticles.

12. The microencapsulated active agent of claim 11, wherein the selecting step (c) is carried out to select no intermediate drying, thereby resulting in microparticles having an initial burst and a substantially linear release profile.

13. The microencapsulated active agent of claim 11, wherein the selecting step (c) is carried out to select substantially complete intermediate drying, thereby resulting in microparticles having an initial lag phase and a substantially sigmoidal release profile.

14. The microencapsulated active agent of claim 11, wherein the method further comprises after step (c):
    (e) performing the selected degree of intermediate drying.

15. The microencapsulated active agent of claim 14, wherein the substantially complete intermediate drying results in the microparticles having a moisture content of less than about 0.2% after step (e).

16. Microparticles prepared by the method of claim 1.

17. Microparticles prepared by the method of claim 3.

18. Microparticles prepared by the method of claim 7.

* * * * *